United States Patent [19]

Englemann et al.

[11] 4,286,054
[45] Aug. 25, 1981

[54] LIGHT SENSITIVE, COLOR PHOTOGRAPHIC SILVER HALIDE COMPOSITIONS WITH DIR-COUPLERS

[75] Inventors: Horst Englemann, Wolfen; Rainer Redmann; Monika Bethke, both of Dessau; Christa Melz, Delitzsch; Gerd West; Jürgen Mistol, both of Dessau; Udo Sydow, Leipzig, all of German Democratic Rep.

[73] Assignee: VEB Filmfabrik Wolfen, Wolfen, German Democratic Rep.

[21] Appl. No.: 154,245

[22] Filed: May 29, 1980

[51] Int. Cl.³ ............................................. G03C 1/40
[52] U.S. Cl. ................................. 430/544; 430/382; 430/505; 430/553; 430/555; 430/557; 430/558
[58] Field of Search ............... 430/382, 544, 553, 555, 430/557, 558, 505

[56] References Cited

U.S. PATENT DOCUMENTS

| | | | |
|---|---|---|---|
| 3,227,554 | 1/1966 | Barr et al. | 430/382 |
| 3,632,373 | 1/1972 | O'Connell et al. | 430/382 |
| 3,703,375 | 11/1972 | Groet et al. | 430/505 |
| 3,935,015 | 1/1976 | Arai et al. | 430/505 |
| 4,021,248 | 5/1977 | Shiba et al. | 430/554 |
| 4,183,752 | 1/1980 | Kuffner et al. | 430/554 |

*Primary Examiner*—J. Travis Brown
*Attorney, Agent, or Firm*—Jordan and Hamburg

[57] ABSTRACT

A light-sensitive, color photographic silver halide multilayer material contains for the improvement of definition, grain and color rendition DIR-couplers which are substituted in coupling position by mercapto-azole-, mercaptobenz-azole- or mercapto-azine moieties, which themselves carry hydrophilic substituents. The DIR-couplers according to the invention may be used together with other couplers and additives or as sole color forming element and are noteworthy for their high color yields, inter- and intra-image effects. They may be added as well in hydrophobic state (in dispersed form) as in hydrophilic state (as alkaline solutions) and they may be used in single layers or as associated layers with a maximum three layers of a color forming unit and the layers may be arranged in any desired order within the whole combination of layers.

15 Claims, No Drawings

LIGHT SENSITIVE, COLOR PHOTOGRAPHIC SILVER HALIDE COMPOSITIONS WITH DIR-COUPLERS

BACKGROUND OF THE INVENTION AND PRIOR ART STATEMENT

This invention relates to a light sensitive, color photographic silver halide compositions which contain new DIR couplers in order to improve their color rendition and detail rendition.

It is known that one may add to light sensitive silver halide color photographic materials color couplers for the improvement of the quality of the image, which free development inhibitors during the color development proportional to the exposure. They are usually called DIR-couplers ("DIR" meaning "development inhibitor releasing") and are described in detail as to their structure, mechanism of coupling and photographic effect for instance by C. R. Barr, J. K. Thirtle and P. W. Vittum in Phot. Sci. Engn. 13, 274–79 (1969) and in U.S. Pat. No. 3,148,062. Photographic properties which can be improved with DIR-couplers are edge sharpness, color grain and color rendition.

These effects are based upon the diffusion of the freed inhibitor within that layer which contains the DIR-coupler (intra-image effect) and upon the diffusion into the adjacent layer (inter-image effect). The intra-image effect improves the rendition of detail and the inter-image effect may be used for color correction of undesired color layers of image coloring dyes. These effects based upon inhibiting effect and upon diffusion are described by, among others, W. T. Hanson and C. A. Horton in J. Optical Soc. America 42, 633–669 (1952); A. Thiele in Z. Wiss. Photogr., Photophys., Photochem. 47, 105–118 as well as 246–255 (1952) and in Federal Republic of Germany Offenlegungsschrift No. 2,509,722. Furthermore the DIR-couplers may be used according to U.S. Pat. No. 3,620,747 for control of gradation and, in connection with that, for the increase of the brightness of the coloring dyes and, also according to Federal Republic of Germany Offenlegungsschrift No. 2,533,176 for the reduction of development fog, particularly for work at elevated temperatures. The chemical structure of the known DIR-couplers embraces particularly acylacetanilide-, pyrazolone- (5)-, phenol-, or 1-naphthol-derivatives bonded to a usual diffusion-preventing ballast group and in coupling position to a splittable inhibitor group. Particularly effective DIR-couplers carry heterocyclic mercaptoazols, -azines, arylmercaptors or mercapto-carboxylic acids as splittable groups. The most typical diequivalent substituents are 2-nitro-, or 2-aminophenylthio-, benzthiazole-2-ylthio-, 1-phenyl-tetrazole-5-ylthio-, 5-phenyl-1,3,4-oxadiazole-2-ylthio- or benzoxazole-2-ylthio-groups. Syntheses of a multitude of DIR-couplers carrying the typical inhibitor groups are described in, among other places, U.S. Pat. Nos. 3,148,062, 3,227,551, 3,227,554 and in Federal Republic of Germany Offenlegungsschrift No. 2,247,496. The use of prior art DIR-couplers exhibits, though, certain disadvantages. Usually they cannot be used as the single coloring element because the strong inhibiting action of the splitting group retards the chromogenic development so strongly that even development at high temperature results in low saturated images. That necessitates the mixing in of coloring couplers which result in dyestuffs of the same absorption range at a higher yield. Examples of mixtures with two to seven different color couplers and DIR-compounds are shown in U.S. Pat. No. 3,703,375 or Federal Republic of Germany Offenlegungsschrift No. 2,530,645, and their influence upon improvements of definition, grain and color rendition are tabulated. Mixtures contain usually less than 10% of the above-described DIR-couplers. Mostly only incomplete decoupling of the DIR-coupler occurs due to this low concentration of coupler and also because the admixed color coupler exhibits in most cases a higher coupling speed. That leads to low concentrations of freed development inhibitor, in order to render possible particularly efficient inter-image effects by diffusion into adjacent layers. Therefore, special uses of known DIR-couplers are made, for example, in intermediate layers and auxiliary layers, which solely serve to correct color by the interimage effect. They are, for example, described in U.S. application No. 454,525, U.S. Pat. No. 3,006,759 and in Federal Republic of Germany Offenlegungsschrift Nos. 2,421,544 and 2,429,250 and are named also IIC-, ILC- or IIE-couplers. The use of higher concentrations of the known DIR-couplers is furthermore limited by the lowering of the sensitivity and gradation by the so-called "clearing effect." It always occurs when freeing of the inhibitor not proportional to illumination occurs before or during the chromogeneous development or when inappropriate purification methods do not succeed in bringing the residual inhibitor content of the DIR-couplers below 0.5%. Adequate purification is technically difficult and expensive and is sometimes very difficult, if not impossible, to achieve on a commercial scale. As an expedient serve complicated systems of layer construction, as claimed for example in U.S. Pat. Nos. 3,620,745, 3,620,747, Federal Republic of Germany Offenlegungsschrift Nos. 2,322,165, 2,421,544, 2,423,250 and 2,530,645. Here known DIR-couplers are introduced into the insensitive silver halide layers of variously constructed layer units of a color forming element in order to improve image definition and color rendition.

Besides the hereabove described DIR-couplers with thio-ether splittable groups of high inhibitor effect, U.S. Pat. No. 3,617,291 mentions, among others, DIR-couplers which have heterocyclic imino-compounds or precursors thereof which could serve as splittable groups. Typical couplers contain benztriazolyl- or nitrobenzimidazolyl- moieties or derivatives thereof. Compared to the aforementioned DIR-couplers having thioether structure, these compounds show too small DIR-effects and are less capable of color correction effects. It might be also disadvantageous that the known DIR-couplers are mostly hydrophobic compounds and that only rarely the usual inhibitor moieties are bound as splittable groups to hydrophilic compounds. They only can be used for photographic material when dispersed, which means an addition of high- or sometimes low-boiling solvents and emulsifiers, which is more expensive than the use of a simple solution.

It is an object of the invention to make possible by the use of new DIR-couplers the preparation of color photographic silver halide multilayer materials of good definition, grain and color rendition, avoiding the disadvantages of present technical solutions such as, for instance, too low intra- and inter-image effects due to a too small DIR-coupler percentage in mixtures with other couplers or the use of a complicated layer construction for a color photographic multilayer material or high costs of production caused by a complicated purification process for the DIR-couplers which are being used. Another aim of the invention is to lower the costs of the aforementioned silver halide materials by using new DIR-couplers which may be added to the color photographic silver halide layers as aqueous alkaline solutions.

SUMMARY OF THE INVENTION

According to the invention there are provided new DIR-couplers which may be added in high concentration in order to obtain efficient intra- and inter-image effects, which need little purification efforts when prepared, show high stability in the photographic layer and only negligible or no desensitizing effects and which may be added as well in dispersions as in aqueous alkaline solutions. According to the invention this task is fulfilled by using as DIR-couplers compounds of the general formula I or II.

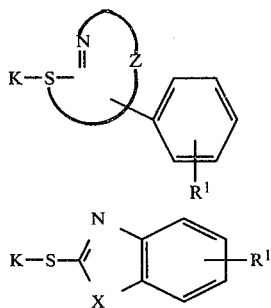

in which
K a color-forming group containing a diffusion preventing moiety and optionally having a substituted acylacetanilide-, 1-arylpyrazolone-(5)-, 1-naphthol- or phenol-structure and where the hydrophilicly substituted inhibitor splittable group is bound at a coupling position,
Z atoms or atomic groups for the completion of a heterocyclic 5- or 6-ring,
X O, S, NR$^2$
R$^1$ —OR$^3$, —COOR$^3$, —SO$_2$NHR$^3$, —SO$_3$R$^3$,
R$^2$ H-atom or an alkyl moiety with a maximum of 5 C-atoms and
R$^3$ H-atom or an ammonium- or metal-ion.

The yellow-, purple- and bluegreen-DIR-couplers according to the invention consist of a coupler moiety and a thio-ether or tautomer thio-imido splittable group. It is of decisive importance for the photochemical effect of the invention that the splittable group be a mercapto-azol or azine or a benzcondensed derivative thereof carrying a hydrophilic group R$^1$.

The DIR-couplers according to the invention are very well suited for the improvement of the precision, color grain and color rendition of light-sensitive color photographic multilayer materials. They are distinguished by their remarkable range of dosage. They may be added in relatively high concentrations to individual silver halide layers in a proportion up to 50% relative to a colorcoupler for the same spectral range of the eventual image coloring material or in some cases even may be used as sole color forming element. The DIR-coupler may be added to silver halide dispersions in amounts between 1 and 100 g. per mole silver halide. When used in high concentrations up to its use as the sole color forming element, the amount is between 30 and 100 g. per mole silver halide.

The DIR-couplers of the invention may be used in addition to any other coupling compounds such as color couplers, masking couplers and colorless couplers in amounts from 1 to 30 g. per mole silver halide. The use at high concentrations guarantees good coupling, assuring color yields above 50% and simultaneously also the freeing of large amounts of development inhibitor causing effective intra- and inter-image effects.

Excellent intra-image effects can be found within the layer, which are easily recognized by fine grain and good definition. Due to the high local concentration after the coupling reaction large amounts of development inhibitor can diffuse into adjacent layers. Thus the DIR-couplers according to the invention allow, for instance, an efficient correction of the incident color densities of the image dyestuffs in the adjacent layers due to the incident color densities of the image dyestuffs in the adjacent layers due to the inter-image effect in a relatively simple layer construction of the color photographic material. These advantages of the couplers according to the invention are obviously caused by the fact that they contain as thio-ether splittable groups mercapto-azoles or mercapto-azines or respective benzocondensed derivatives thereof which contain a hydrophilic group R$^1$.

Kinetic measurements suggest that the efficient coupling together with high color yields compared to the heretofore known DIR-couplers is not caused by a higher speed of the color coupling process but by the specially advantageous inhibitor effects of the hydrophilic substituted thio-ether splittable groups contained by the DIR-couplers. These effects are largely independent of the type of the coupler K in the general formulas I and II of the DIR-coupler according to the invention. The execution of the kinetic investigation and the results of the measurements are shown in Table 2.

An additional advantage of the use of the DIR-couplers according to the invention is that small amounts of the respective unreacted hydrophilic substituted mercapto-heterocyclic compounds exhibit considerably lower losses of sensitivity than was the case with prior art DIR-couplers. Thus, there is less need for purification as compared with prior art DIR-couplers. The DIR-couplers according to the invention are furthermore excellently stable within a photographic layer and show no diminution of sensitivity due to splitting not proportional to illumination.

An added advantage of the invention is that the new couplers may be added to a photographic emulsion according to one of the usual dispersing methods, for instance as disclosed in Federal Republic of Germany Offenlegungsschrift No. 1,261,061, or as a solution. The solution is an alkaline medium containing a dipolar aprotic solvent, for instance DMF (see "Introduction Examples" 1 to 3).

The DIR-couplers of the invention may be used along with other photochemical additives such as gelatine substitutes, hardeners, wetting agents, chemical and spectral sensitizers, stabilizers and clarifying agents, antioxidants, compounds for pH-regulation and so forth. Furthermore, the DIR-coupler of the invention may be used regardless of the constitution of the silver halide, its crystal structure and habitus, the base of the film, the constitution of the binder and the use of additional materials which aid in the preparation of silver halide multilayer materials. The DIR-couplers according to the invention may be used in photographic material in single layers or in multiple-layer constructions. The order of the layers in photographic materials which contain these DIR-couplers in single layers and in photographic materials which contain DIR-couplers in multiple layers is immaterial.

Some structures of the new compounds are shown in Table 1. These cited examples of DIR-couplers with hydrophilicly substituted inhibitor splittable groups in coupling position of prior art yellow-, purple- and blue-green color couplers do not limit the scope of the invention. They are produced according to the "Synthesis Examples" 1 to 3 or in an analogous manner. The principle of synthesis is to couple at 50° to 150° C. in a dipolar aprotic solvent the alkali salts of hydrophilic substituted mercapto-azoles to the respective color couplers which are halogen substituted in their coupling position. Synthesis of the mercapto-azoles may be performed in the case of hydrophilic substituted mercapto-azoles according to German Democratic Republic Patent No. 80,625. Table 1 shows the structures, their melting-points and the synthesis yields.

TABLE 1

| No. of Compound | Melting Point (Yield in %) | Structure |
|---|---|---|
| 1 | 134–135 (32) | 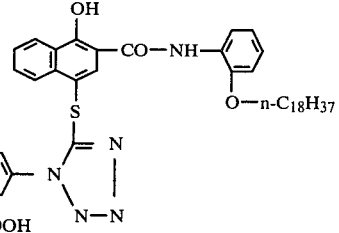 |
| 2 | 121–123 (46) | 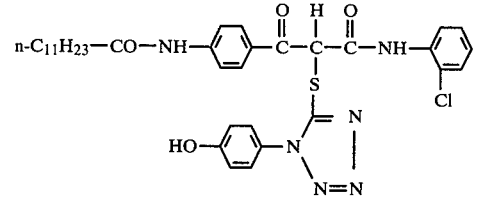 |
| 3 | 125–128 (30) | 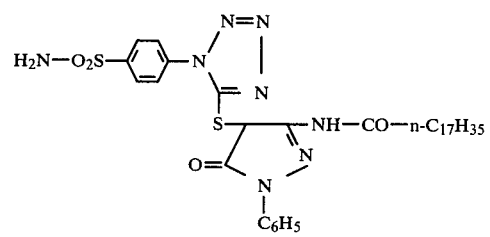 |
| 4 | 164–166 (45) | 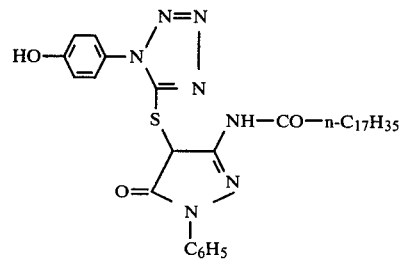 |
| 5 | 96–103 (34) | 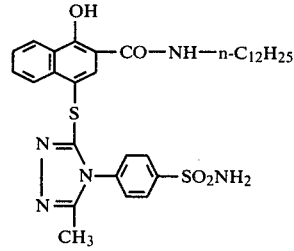 |

TABLE 1-continued
| No. of Compound | Melting Point (Yield in %) | Structure |
|---|---|---|
| 6 | — (18) | 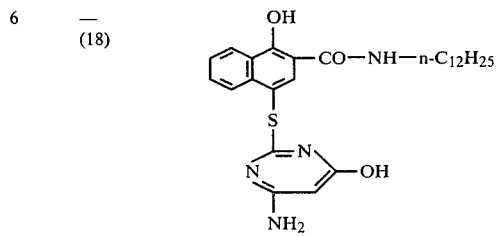 |
| 7 | — (42) | 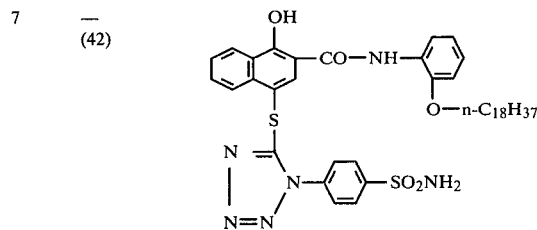 |
| 8 | 173–176 (24) | 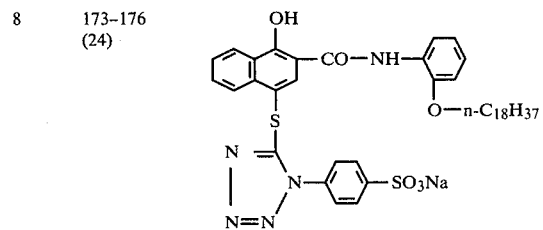 |
| 9 | — (28) | 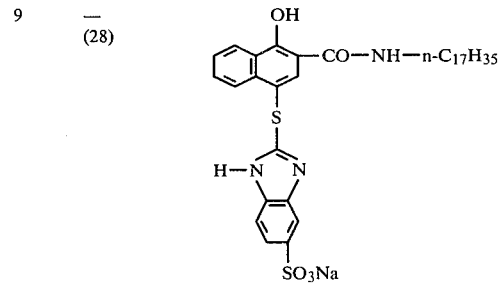 |
| 10 | 184 (35) | 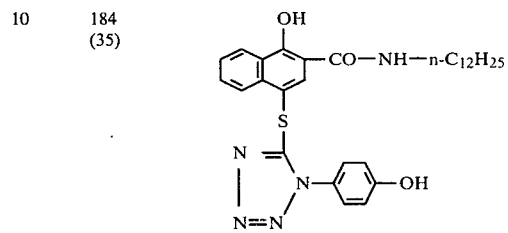 |
| 11 | 130 (42) | 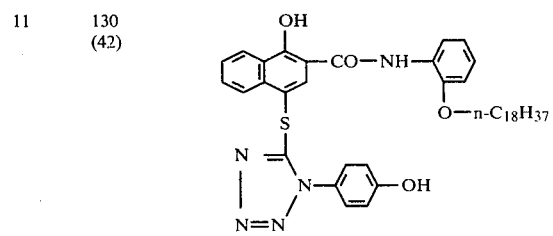 |

TABLE 1-continued

| No. of Compound | Melting Point (Yield in %) | Structure |
|---|---|---|
| 12 | 191-193 (21) | 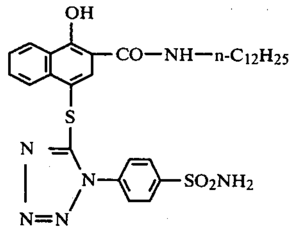 |

Kinetic investigations were performed on known DIR-couplers (compound Nos. 13 and 14 in Table 2) which were synthesized analogously to the synthesis examples in U.S. Pat. No. 3,227,551 and which contain the known 1-phenyltetrazole-5-yl-thio- moiety as a splittable group, and were also performed on compounds 7 and 10 (Table 1) of the invention, which differ from compounds 13 and 14 by the hydrophilic groups in the splittable groups. The reactions between these DIR-couplers and the oxidation product of N,N-diethyl-p-phenylenediamine were performed at 25° C. in aqueous n-propanol. The dye formation follows the kinetic law of the second order and the rate of reaction is characterized by the rate constant $K_2$, whose numerical values can be found in Table 2. The reaction rates of the compounds 13 and 10 or 14 and 7, belonging to the same type of couplers, respectively, differ only slightly and are in the same range. The DIR-couplers according to the invention show no greater reaction rates than the known DIR-couplers. (See Table 2.)

TABLE 2

| No. of the Compound | $R^1$ | $R^2$ | $K_2$ |
|---|---|---|---|
| 13 | 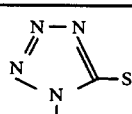 | n-C$_{12}$H$_{25}$ | $1.4 \times 10^4$ |
| 10 |  | n-C$_{12}$H$_{25}$ | $1.1 \times 10^4$ |
| 14 |  | 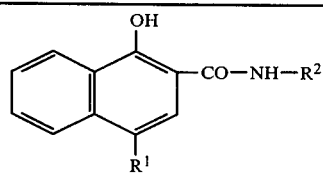 | $2.9 \times 10^5$ |
| 7 | 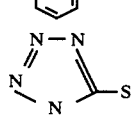 |  | $1.3 \times 10^5$ |

DETAILED DESCRIPTION OF PREFERRED EMBODIMENT

Operating Examples

Synthesis example 1

4-[1-(3-carboxyphenyl)-tetrazole-5-yl]-mercapto-1-hydroxy-2-naphthoic acid-(2'-octadecyloxy)-anilide (Compound 1)

4.88 g (0.02 mol) Na-salt of 1-(3-carboxyphenyl)-5-mercapto-tetrazole and 12.2 g (0.02 mol) 4-bromo-1-hydroxy-2-naphthoic acid-(2'-octadecyloxy-)-anilide are heated eight hours under reflux in 200 ml. boiling acetone. The solvent is distilled off, the residue is taken up in 500 ml. boiling ethanol and separated from sodium bromide by filtration, while hot. After standing 6 to 10 hours at a temperature of 0° to 10° C., Compound 1 crystallizes. The supernatant liquid is sucked off, and the crystals are washed with ice cold ethanol and air-dried. yield=4.9 g (1×ethanol)=32% of theoretical; melting point 134° to 135° C.

Synthesis example 2

3-stearoylamino-4-[(1-p-hydroxyphenyl)-tetrazole-5-yl]-1-phenylpyrazolone-(5) (Compound 4)

Analogously to Synthesis Example 1, 4.32 g. (0.02 mol) Na-salt of 1-p-hydroxyphenyl-5-mercaptotetrazole is reacted with 9.52 g (0.02 mol) 5-chloro-3-heptadecyl-carbamoyl-1-phenylpyrazolone-(5). yield=5.7 g (1×ethanol)=45% of theory; melting point 164° to 166° C.

The 5-chloropyrazolone needed is prepared as follows:

44.16 g (0.1 mol) 3-stearoylamino-1-phenyl-pyrazolone-(5) is stirred in 500 ml. absolute methylene chloride at 0° to 10° C. under exclusion of moisture. 9.5 ml (0.12 mol, sp. gr. =1.667 g/cm$^2$) sulfurylchloride in 25 ml. absolute methylene chloride is added dropwise. After stirring for half an hour, the mixture is boiled 4 hours under reflux. The solvent is distilled off, the residue is recrystallized 1× from methanol and 1× from acetone. yield=24.4 g.=51.3% of theoretical; melting point 52° to 55° C.

Synthesis Example 3

2-(p-lauroylaminobenzoyl)-2-(1-p-hydroxy-phenyltetrazole-5-yl)-mercapto-(o-chloro)-acetanilide (Compound 2) Analogously to Synthesis Example 1, 4.32 g. (0.02 mol) Na-salt of 1-(p-hydroxyphenyl)-5-mercaptotetrazole are reacted with 10.12 g (0.02 mol) 2-chloro-2-(p-lauroylamino)-benzoyl-(o-chloro)-acetanilide. An an intermediate product the respective 2-chlorobenzoylacetanilide was prepared according to the method "chlorination with sulfurylchloride in methylene" analogously to Synthesis Example 2. yield=7.2 g. (1×ethanol)=76% of theoretical; melting point 142° C.

The following "Addition Examples" show that, for example, the DIR-coupler compound 7 may be used in a form allowing the addition to a photographic emulsion. It may be used in an alkaline solution or in a dispersion.

Addition Example 1

5.3 g. (0.01 mol) of Compound 13 are dissolved in 17.5 ml ethyl acetate and 2.5 ml. dibutylphthalate at elevated temperature. The dispersing beaker contains at 40° to 60° C. 53 ml. 10% aqueous gelatine solution and 10 ml. 5% dodecylsulfonate aqueous solution. The coupler solution is poured hot into the beaker and stirred 3 minutes.

Subsequently, ethyl acetate is distilled off under vacuum and the residue is stabilized by the addition of 4 ml. aqueous phenol solution. The dispersion is congealed, chopped and kept in the refrigerator.

Addition Example 2

7.87 g. (0.01 mol) Compound 7 is dissolved in a warm mixture of 5 ml. dimethylsulfoxide, 10 ml. methylene chloride, 5 ml. dibutyl phthalate and 10 ml. ethyl acetate and added to a mixture of 79 ml. of 10% aqueous solution of gelatine and 15 ml. 5% aqueous dodecyl sulphonate. Further processing is according to Addition Example 1.

Addition Example 3

7.87 g. (0.01 mol) DIR-coupler Compound 7 is dissolved at 50° C. in 6 ml. dimethylformamide. 11 ml. (0.022 mol) 2 N NaOH is added while stirring, the solution is filtered if impurities precipitate and water is added up to the desired volume.

The following examples demonstrate the advantages when using the DIR-couplers according to the invention. As a comparison for the present state of the art Compound 13 (U.S. Pat. No. 3,227,551) is being used.

EXAMPLE 1

A high sensitivity gold ripened silver bromideiodide high temperature emulsion, containing 25 g. silver per kg. emulsion, 6 mol% iodine and having an average grain size of 0.5 micrometer is sensitized by the addition of $7.10^{-4}$ mol 3-ethyl-3'-sulfoethyl-5,5'-dimethyl-9-ethylbenzthiotrimethine-cyaninebetaine per mol silver and divided in four parts.

Part A contains 0.15 mol 1-hydroxy-naphthoic acid(2)-[2-(n-octadecyl-methyl-amino)-5-sulpho]-anilide per mol silver and is designated "Typ."

Part B contains 0.15 mol Compound 13 per mol silver and represents the state of the prior art.

Part C contains 0.15 mol Compound 12 per mol silver according to the invention.

Part D contains 0.15 mol Compound 8 per mol silver according to the invention.

After the addition of the conventional additives, the emulsion samples are poured onto a support at a rate of 1 g. silver per m².

Subsequently the samples are exposed under a gray wedge (factor 2) with red light and are processed as follows:

| Specification 1 | | |
|---|---|---|
| 1. color development | 7 min. | 20° C. |
| 2. washing | 15 min. | 12 to 15° C. |
| 3. bleaching | 5 min. | 20° C. |
| 4. washing | 5 min. | 12 to 15° C. |
| 5. fixing | 5 min. | 20° C. |
| 6. washing | 15 min. | 12 to 15° C. |
| color developer: | | |
| lime protector | 3 | g. |
| hydroxylamine sulphate | 1.2 | g. |
| diethyl-p-phenylenediamine-sulphate | 2.75 | g. |
| potassium carbonate | 75 | g. |
| sodium sulfite | 2 | g. |
| potassium bromide | 2 | g. |
| water to make total volume of | 1 | l. |
| bleach bath: | | |
| Potassium cyanoferrate (III) | 40 | g. |
| potassium dihydrogen phosphate | 25 | g. |
| potassium bromide | 15 | g. |
| water to make total volume of | 1 | l. |
| fixing bath: | | |
| sodium thiosulphate pentahydrate | 250 | g. |
| sodium tripolyphosphate | 10 | g. |
| water to make total volume of | 1 | l. |

| Specification 2 | | |
|---|---|---|
| 1. color development | 5 min. | 35° C. |
| 2. washing | ½ min. | 35° C. |
| 3. stop bath | 5 min. | 35° C. |
| 4. washing | 5 min. | 35° C. |
| 5. bleaching | 5 min. | 35° C. |
| 6. washing | 5 min. | 35° C. |
| 7. fixing | 5 min. | 35° C. |
| 8. washing | 15 min. | 35° C. |
| color developer | | |
| lime protector | 3 | g. |
| hydroxylamine sulphate | 1.2 | g. |
| diethyl-p-phenylenediamine sulphate | 1.4 | g. |
| potassium carbonate | 50 | g. |
| sodium sulphite | 1 | g. |
| potassium bromide | 2 | g. |
| water to make total volume of | 1 | l. |
| stop bath | | |
| sodium sulfite | 7.5 | g. |
| sodium acetate | 15 | g. |
| acetic acid (concentrated) | 25 | g. |
| potassium aluminum sulphate (dodecahydrate) | 25 | g. |
| sodium thiosulphate | 200 | g. |
| water to make total volume of | 1 | l. |
| For bleach and fixing bath see specification 1. | | |

The photographic results of filmstrips A to D are shown in Table 3 below. The data show that use of the Compounds 8 and 12 of the invention lead to considerably higher yields of dyestuff in comparison to Compound 13 according to the prior art.

Compound 12 in comparison to Compound 13 exhibits in both specifications a slight diminution of sensitivity.

EXAMPLE 2

A color photographic multilayer material I contains the following layers:

1. As a base coat, the formulation described in Example 1, part A is used and poured onto a carrier which is provided on its emulsion side with a reflection antihalation layer.
2. A gelatine interlayer.
3. For the intermediate layer the same emulsion as for the base coat is to be used, but spectrally sensitized by adding $2.5 \cdot 10^{-4}$ mol 3,3'-bis-[$\beta$-sulphatoethyl]-5,5'-diphenyl-9-ethyl-benzoxotrimethinecyaninebetaine per mol silver.

Besides the conventional coating additives 0.12 mol 1-phenyl-3-stearoylpyrazolone-5 is added per mol silver as purple coupler.

4. A yellow filter layer consisting of gelatine and colloidal silver.
5. As a top layer a high sensitivity silver bromide iodide emulsion is used having an average grain size of 0.7 micrometer, an iodine content of 5 mol% and a silver content of 27 g. per kg. of emulsion. As a yellow coupler are used 0.16 mol 4-stearoylamino-benzoylacet-[2-3',5'-carboxyphenoxy)-5-carboxy]-aniline.
6. A gelatine coating.

A second photographic multilayer material II is prepared like I but contains in its base coat instead of the aforementioned bluegreen couplers 0.15 mol Compound 12 per mol silver. Silver is applied at a rate of 2 g./m². Both materials are exposed to light of a color temperature of 3200° K. under a gray wedge (factor 2) and worked up according to Specification 2. Table 4 below shows the photographic results. The inter-image effects were calculated using the method described in Federal Republic of Germany Offenlegungschrift No. 2,509,722.

$$IIE = (\gamma_s - \gamma_w / 0.6) \cdot 100 [\%]$$

$\gamma_s = \gamma$ at selective illumination
$\gamma_w = \gamma$ at white illumination
IIE is evaluated from base coat to middle coat. Its value is Multilayer material I = 2%
Multilayer material II = 17%

In order to evaluate graininess the multilayer materials I and II were exposed up to density 1 and developed. Graininess was evaluated visually at 10× magnification. It was found here that material II is finer grained than material I, both exhibiting the same densitometric data (see Table 4)

EXAMPLE 3

A third photographic multilayer material III is prepared like I but contains in its base coat per mol silver 0.15 mol 1-hydroxy-naphthoic acid-(2)-[2-(n-octadecyl-methylamino-5-sulpho]-anilide and 0.04 mol of Compound 12 with 2 g. silver per m². The materials I and III were exposed (3200° K.) and worked up according to Specification 1. Material III exhibits, in comparison to material I, a desired lowering of gradation in the middle layer (see Table 5 below) and an obviously improved IIE of 35%, while material I shows only an improvement of 2%. Copies of material III show improved color rendition compared to material I.

EXAMPLE 4

A fourth photographic multilayer material IV is prepared as follows:

1. A double layer unit is used as a base coat. It consists of a non-sensitive layer nearer to the carrier with the reflection antihalation layer with a gold-ripened silver bromide iodide high temperature emulsion of 0.4 micrometer average grain size, a silver content of 20 g. per kg. emulsion and an iodide content of 4 mol% and a superimposed layer with a more sensitive silver bromide iodide high-temperature emulsion of 0.6 micrometer average grain size, a silver content of 25 g. per kg. emulsion and an iodine content of 6 mol%. Both layers are sensitized by the addition of $7 \cdot 10^{-4}$ mol per mol silver 3-ethyl-3-sulfoethyl-5,5'-dimethyl-9-benzthio methinecyaninebetaine. The less and more sensitive layers contain per mol silver 0.15 mol and 0.04 mol, respectively, 1-hydroxy-naphthoic acid-(2)-[2-(n-octadecyl-methyl-amino)-5-sulpho]-anilide. Both layers are coated with silver at a rate of 0.7 g. per m².
2. A gelatine intermediate layer.
3. The middle layer consists of a unit of two layers. The emulsions used relate to the layers in the base coat. Both of the middle layers are spectrally sensitized with $2.5 \cdot 10^{-4}$ mol 3,3'-bis[-sulphatoethyl]-5,5-diphenyl-9-ethyl-benzoxotrimethinecyaninebetaine. The less sensitive layer, which lies closer to the support, contains 0.08 mol 1-phenyl-3-stearyl-pyrazolone-(5) and 0.06 mol 1-(4'-phenoxy-3'-sulpho)-phenyl-3-stearoylamino-4-[(-4'''-methyl-phenylsulphonyl)-4''-aminophenylazo]-pyrazolone-(5). The more sensitive layer contains 0.04 mol 1-phenyl-3-stearyl-pyrazolone-(5) per mol of silver.

A photographic multilayer material V is prepared like IV but contains according to the invention in the leass non-sensitive layer of the base coat 0.04 mol of Compound 8 and in the less non-sensitive layer of the middle layer 0.03 mol of Compound 4, calculated per mol silver, the silver content of the respective layers being increased by 30%. The materials IV and V are processed according to Specification 1. The photographic results are shown in Table 6 below. The inter-image effect IIE is:

| | base coat | middle layer |
|---|---|---|
| Material IV | 0% | 0% |
| Material V | 10% | 11% |

Material V has a finer grain when copied shows a better color rendition than material IV.

TABLE 3

| Material | Processing Specification | $\gamma$ | $E_{rel\ 0.1}$ | $D_{min}$ | $D_{max}$ |
|---|---|---|---|---|---|
| A | 1 | 0.60 | 100% | 0.26 | 100% |
| B | 1 | <0.10 | 47% | 0.14 | 8% |
| C | 1 | 0.15 | 32% | 0.18 | 38% |
| D | 1 | 0.20 | 88% | 0.12 | 26% |
| A | 2 | 0.60 | 100% | 0.29 | 100% |
| B | 2 | <0.10 | 22% | 0.24 | 25% |
| C | 2 | 0.24 | 25% | 0.20 | 64% |
| D | 2 | 0.32 | 68% | 0.13 | 56% |

TABLE 4

| Material | | $\gamma$ | $E_{rel\ 0.1}$ | $D_{min}$ |
|---|---|---|---|---|
| I | top coat intermediate | 0.65 | 100% | 0.15 |

TABLE 4-continued

| Material | | γ | $E_{rel\,0.1}$ | $D_{min}$ |
|---|---|---|---|---|
| | coat | 0.61 | 100% | 0.16 |
| | base coat | 0.60 | 100% | 0.20 |
| II | top coat | 0.60 | 95% | 0.18 |
| | intermediate | | | |
| | coat | 0.53 | 95% | 0.12 |
| | base coat | 0.52 | 112% | 0.13 |

TABLE 5

| Material | | γ | $E_{rel\,0.1}$ | $D_{min}$ |
|---|---|---|---|---|
| I | top coat | 0.65 | 100% | 0.15 |
| | intermediate | | | |
| | coat | 0.61 | 100% | 0.16 |
| | base coat | 0.60 | 100% | 0.20 |
| II | top coat | 0.60 | 100% | 0.16 |
| | intermediate | | | |
| | coat | 0.45 | 105% | 0.14 |
| | base coat | 0.50 | 105% | 0.17 |

TABLE 6

| Material | | γ | $E_{rel\,0.1}$ | $D_{min}$ |
|---|---|---|---|---|
| IV | top coat | 0.64 | 100% | 0.80 |
| | intermediate | | | |
| | coat | 0.60 | 100% | 0.24 |
| | base coat | 0.63 | 100% | 0.20 |
| V | top coat | 0.63 | 95% | 0.76 |
| | intermediate | | | |
| | coat | 0.59 | 100% | 0.25 |
| | base coat | 0.57 | 105% | 0.25 |

What we claim is:

1. A light-sensitive, color photographic material including at least one silver halide emulsion layer containing a DIR-coupler being a compound of the formula

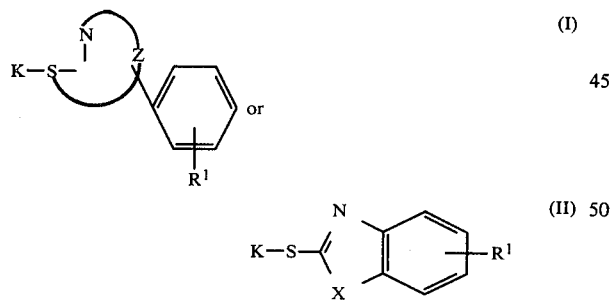

in which
K is a substituted acylacetanilide-, 1-aryl-pyrazolone-(5)-, 1-naphthol- or phenol- structure,
Z is an atom or atom group for the completion of a heterocyclic 5- or 6-member ring
X is O, S, or $NR^2$
$R^1$ is a hydroxyl, carboxyl, sulfamido or sulfo group, in which a hydrogen atom may be substituted by an ammonium or a metal ion, and
in the case of formula (I) the hydrophilic substituted inhibitor splittable group is a moiety of the following structure

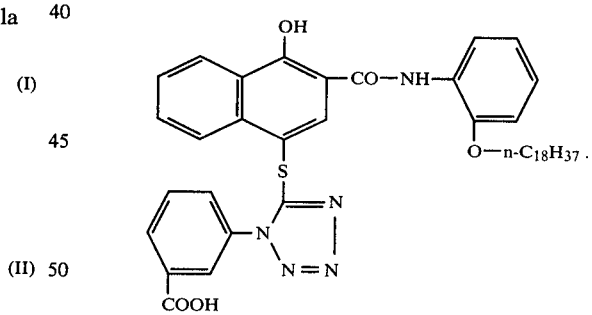

2. A light-sensitive, color photographic material according to claim 1 in which the proportion of the couplers defined in claim 1 is 30 to 100 g. per mol silver halide.

3. A light-sensitive, color photographic material according to claim 1 in which the material also contains other DIR-couplers and the total proportion of the DIR-couplers is 1 to 30 g. per mol silver halide.

4. The material of claim 1 wherein the DIR-coupler is a compound of the formula

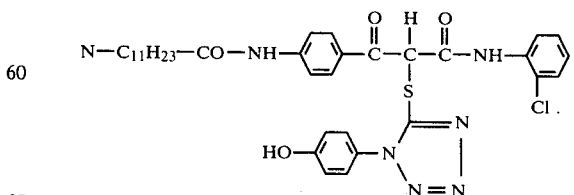

5. The material of claim 1 wherein the DIR-coupler is a compound of the formula $N-C_{11}H_{23}-CO-NH-$⬡$-$C(=O)$-$CH$-$C(=O)$-NH-$⬡$-Cl$ 6. The material of claim 1 wherein the DIR-coupler is a compound of the formula 7. The material of claim 1 wherein the DIR-coupler is a compound of the formula

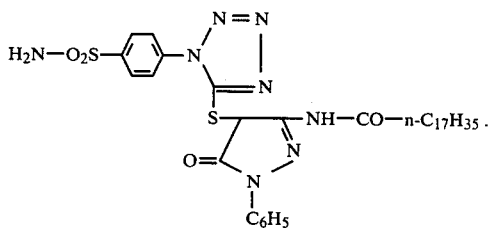

8. The material of claim 1 wherein the DIR-coupler is a compound of the formula

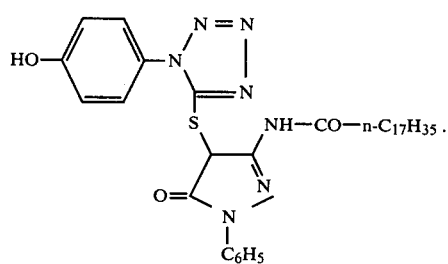

9. The material of claim 1 wherein the DIR-coupler is a compound of the formula

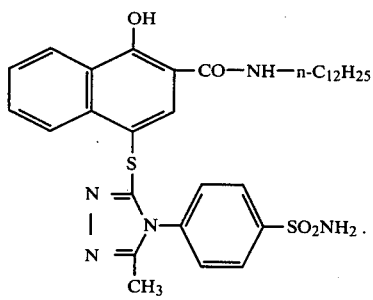

10. The material of claim 1 wherein the DIR-coupler is a compound of the formula

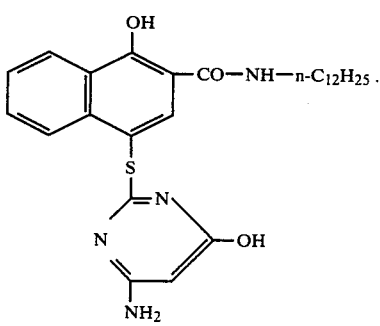

11. The material of claim 1 wherein the DIR-coupler is a compound of the formula

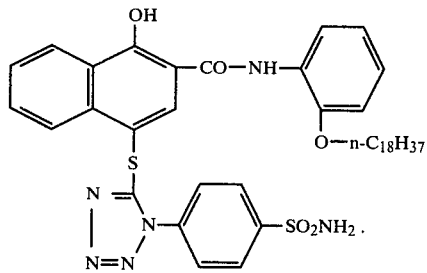

12. The material of claim 1 wherein the DIR-coupler is a compound of the formula

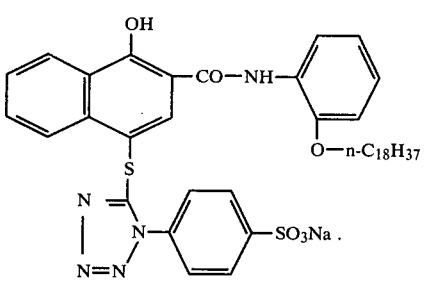

13. The material of claim 1 wherein the DIR-coupler is a compound of the formula

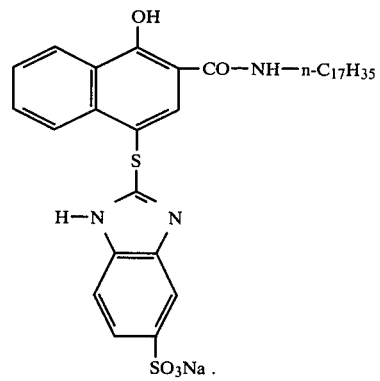

14. The material of claim 1 wherein the DIR-coupler is a compound of the formula

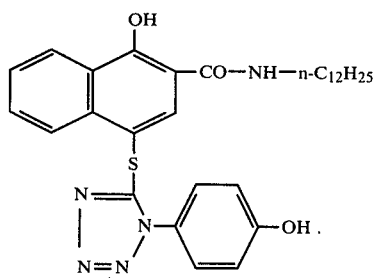

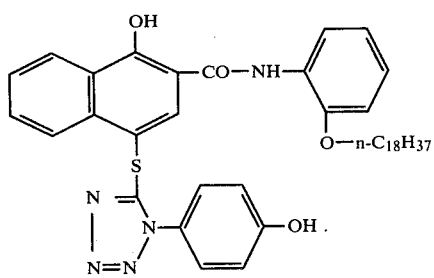
15. The material of claim 1 wherein the DIR-coupler is a compound of the formula
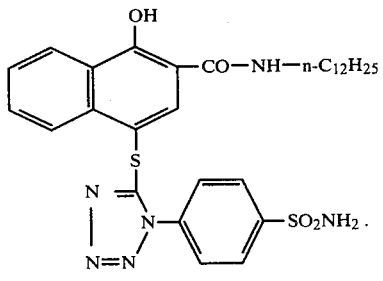
* * * * *

UNITED STATES PATENT AND TRADEMARK OFFICE
CERTIFICATE OF CORRECTION

PATENT NO. : 4,286,054
DATED : August 25, 1981
INVENTOR(S) : Horst ENGLEMANN et al.

It is certified that error appears in the above-identified patent and that said Letters Patent are hereby corrected as shown below:

Claim 1, column 15, after line 65, insert

-- $R^2$ is H-atom or alkyl residue having 1 to 5 C-atoms, and --;

Claims 1, column 15, lines 1-25, in all three formulas change "$R_1$", to -- $R^1$ --.

Signed and Sealed this

Fifteenth Day of December 1981

|SEAL|

Attest:

GERALD J. MOSSINGHOFF

Attesting Officer     Commissioner of Patents and Trademarks

UNITED STATES PATENT AND TRADEMARK OFFICE
CERTIFICATE OF CORRECTION

PATENT NO. : 4,286,054

DATED : August 25, 1981

INVENTOR(S) : Horst Englemann et al.

It is certified that error appears in the above-identified patent and that said Letters Patent is hereby corrected as shown below:

Column 3, lines 21-29, Formula I, change " 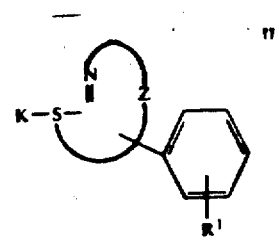 "

to -- 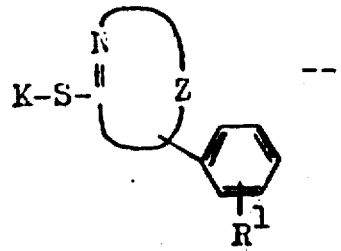 --

UNITED STATES PATENT AND TRADEMARK OFFICE
CERTIFICATE OF CORRECTION

PATENT NO. : 4,286,054

DATED : August 25, 1981

INVENTOR(S) : Horst Englemann et al.

It is certified that error appears in the above-identified patent and that said Letters Patent is hereby corrected as shown below:

Claim 1, column 15, lines 41-49, Formula I, change

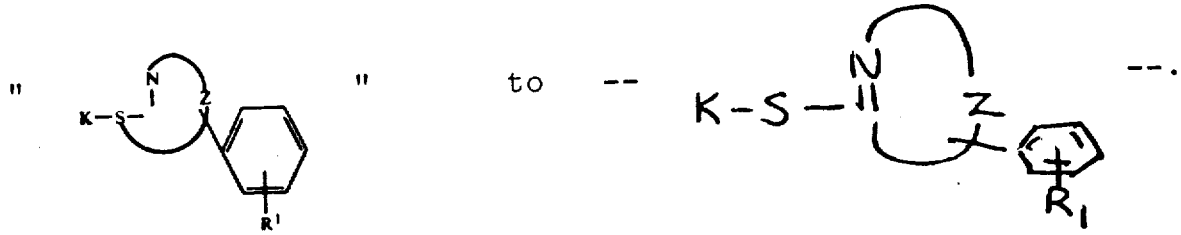

Signed and Sealed this

Tenth Day of August 1982

[SEAL]

Attest:

GERALD J. MOSSINGHOFF

Attesting Officer   Commissioner of Patents and Trademarks